United States Patent [19]

Castronovo et al.

[11] Patent Number: 4,515,766
[45] Date of Patent: May 7, 1985

[54] LABELED PHOSPHONIC ACID COMPOSITIONS FOR INVESTIGATIONS OF IN VIVO DEPOSITS OF CALCIUM

[75] Inventors: Frank P. Castronovo, Burlington; Harry W. Strauss, Newton Center; Majic S. Potsaid, Hanover, all of Mass.

[73] Assignee: The Massachusetts General Hospital, Mass.

[21] Appl. No.: 393,540

[22] Filed: Jun. 30, 1982

Related U.S. Application Data

[63] Continuation-in-part of Ser. No. 162,370, Jun. 23, 1980, abandoned.

[51] Int. Cl.$^3$ .................... A61K 43/00; A61K 49/00; C07F 9/02
[52] U.S. Cl. .................... 424/1.1; 260/502.4 P; 424/9
[58] Field of Search .................... 424/1, 1.5, 9; 260/502.4 P

[56] References Cited

U.S. PATENT DOCUMENTS

| | | |
|---|---|---|
| 3,989,730 | 11/1976 | Subramanian et al. ............... 424/1 |
| 4,104,366 | 8/1978 | Schmidt-Dunker et al. ......... 424/1 |
| 4,115,541 | 9/1978 | Subramanian et al. ............... 424/1 |
| 4,133,872 | 1/1979 | Schmidt-Dunker et al. ......... 424/1 |
| 4,187,284 | 2/1980 | Kolleston et al. ..................... 424/1 |
| 4,229,427 | 10/1980 | Whitehouse ........................... 424/1 |
| 4,232,000 | 11/1980 | Fawzi ..................................... 424/1 |
| 4,233,284 | 11/1980 | Fawzi ..................................... 424/1 |
| 4,234,562 | 11/1980 | Tofe et al. .............................. 424/1 |
| 4,247,534 | 1/1981 | Bevan ..................................... 424/1 |

FOREIGN PATENT DOCUMENTS

| | | | |
|---|---|---|---|
| 0047983 | 3/1982 | European Pat. Off. ............... | 424/1 |
| 1429549 | 3/1976 | United Kingdom ................... | 424/1 |

OTHER PUBLICATIONS

Castronovo et al., from *Radiopharmaceuticals and Labelled Compounds*, IAEA, Vienna, 1973, pp. 79–82.
Wellman et al., from *Radiopharmaceuticals and Labelled Compounds*, IAEA, Vienna, 1973, pp. 93–108.

Primary Examiner—Christine M. Nucker
Attorney, Agent, or Firm—Paul J. Cook; Marvin C. Guthrie

[57] ABSTRACT

The composition and methodology associated with the formulation of a halogenated phosphonic acid labeled in the ring moiety are disclosed having the formula:

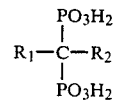

wherein $R_1$ is aryl and is labeled with a halogen and $R_2$ is hydrogen, alkyl, alkenyl, amino, benzyl, hydroxyl—$CH_2PO_3H$ —$CH_2CH_2PO_3H_2$ and is labeled with halogen. The compositions are especially useful for scanning investigations of in vivo deposits of calcium.

16 Claims, No Drawings

LABELED PHOSPHONIC ACID COMPOSITIONS FOR INVESTIGATIONS OF IN VIVO DEPOSITS OF CALCIUM

REFERENCE TO RELATED APPLICATION

This application is a continuation-in-part of U.S. Ser. No. 162,370, filed June 23, 1980, abandoned.

BACKGROUND OF THE INVENTION

This invention relates to phosphonic acid compositions for investigations of in vivo deposits of calcium and their use for diagnosis by scanning and for therapy by concentrating sufficient radioactivity in areas of skeletal pathology (metabolic, primary cancers, metastases). Scanning is defined to include emission studies (photon, NMR, X-ray Fluorescence) and transmission studies (convention X-ray, transmission tomography).

At the present time, there are a wide variety of radioactive compositions which, when administered to a human, will accumulate in specific organs, tissues or sketetal material. After administration, radiation detection apparatus are used to visualize the target areas to monitor the function of the organ, tissue or skeletal material.

Presently, there are available a wide variety of phosphorous compounds which have been radiolabeled with technetium in order to produce radiolabeled compounds which are specific to deposition in the skeleton. Exemplary compounds are disclosed, for example, in U.S. Pat. Nos. 3,735,001, 3,931,396, 3,947,268, 3,984,531, 3,989,730, 4,016,249, 4,233,284 and 4,234,502. All of these compounds are labeled with technetium-99m. It is desirable to utilize technetium-99m as a radiolabel since it has high specific activity which makes possible visualization of the entire skeleton, yet the radiation is easily collimated. Technetium-99m also has a relatively rapid rate of decay of about 6 hr half-life which makes it useful for many diagnostic purposes. In addition, the decay product (technetium-99m) has low radiation levels which renders it safe for use in patients. Also, technetium-99m is readily available from molybdenum-99m generators.

While technetium-labeled bone seeking complexes are suitable in scintigraphy, their use is limited to determining the condition of the skeletal structure for only a short period corresponding to the decay characteristics for technetium-99m, usually only for about 6 hr. In many cases, it is desirable to monitor the condition of the skeletal structure for a longer period, so that the long term effects of a particular treatment on or the natural healing rate of a particular portion of the skeletal structure can be monitored over relatively long periods such as 60 days or more.

Prior to the present invention, there has not been available a substrate which, after labeling with a suitable radionuclide, would afford short and long term analysis of skeletal metabolism. Complexes which afford analysis by scanning over short time periods corresponds to the physical decay of technetium-99m and those suitable for long time analysis include complexes labeled with radionuclides with longer physical half-lives. The latter include halogens consisting of iodine-123, iodine-125 and iodine-131.

It would be desirable to provide scanning agents which are highly selective in their affinity for in vivo calcium deposits (such as the skeleton) as compared to other parts of the body. Furthermore, it would be desirable to provide such scanning agents that would permit both short term and long term monitoring of changes in calcium metabolism without harm to the patient. Such scanning agents then would provide a means for comparing changes in calcium metabolism in normal and diseased states.

SUMMARY OF THE INVENTION

The composition and methodology associated with the formulation of a halogenated phosphonic acid which is labeled in the ring moiety are disclosed. The compositions are especially useful for scanning investigations of in vivo deposits of calcium (e.g., the skeleton, myocardial infarcts).

These compositions are adminstered parenterally to a human and the biodistribution of the labeled composition is monitored by scanning in order to follow the progress of skeletal material or other portions of the body wherein calcium ion is absorbed or desorbed either normally or in a diseased state. A kit also is provided which includes aryl-methylene hydroxy diphosphonic acid, and, when radiolabeling with technetium-99m, a suitable reducing agent for reducing technetium-99m from Tc(VII) to Tc(IV). The kit also may include a chromatographic column containing material capable of binding technetium as the pertechnetate, or as a complex of technetium as well as being capable of binding a reducing agent which reduces technetium (VII) to technetium (IV). When radiolabeling with iodine, the kit also includes a solution of radioactive iodine either alone or admixed with an oxidizing agent for iodine either in a separate vial or admixed therewith. The kit also may contain a chromatographic column to effect purification of the radiolabeled phosphonic acid.

DESCRIPTION OF SPECIFIC EMBODIMENTS

A scanning agent labeled with a stable or a radioactive halogen or a dual label consisting of technetium-99m and the halogen of the formula:

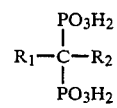

wherein: $R_1$ is aryl (e.g., phenyl, naphthyl) phenylhydroxy, phenylethyl, benzyl; and is labeled with a halogen (e.g., iodine, chlorine, bromine, fluorine) and $R_2$ is hydrogen, alkyl, alkenyl, amino, benzyl, hydroxyl, $-CH_2PO_3H$ $-CH_2CH_2PO_3H_2$ and is labeled with halogen (e.g., iodine, chlorine, bromine, fluorine).

The phosphonic acid compounds are labeled either with halogen or with both halogen and technetium-99m. Labeling with technetium-99m occurs at the oxygen groups via coordinate co-valent bonding. Labeling with the halogen, (e.g., iodine) occurs directly on the ring or on a substitute bound to the ring, which ring is in turn bound to the carbon atom.

The preferred compounds are those wherein the phenyl ring is not substituted or is substituted with hydroxy. The aryl-methylene hydroxy diphosphonic can be prepared by the method disclosed in French Pat. No. 1,412,865 to Henkel and Cie.

The labeled compounds of this invention provide substantial advantages over the bone scanning agents of the prior art. The labeled compounds of this invention have been shown to have high selectivity for being bound to the parts of the body having high calcium ion concentration such as normal and pathological skeletal structure, newly formed and mature myocardial infarcts, cerebral infarcts or breast lesions. Furthermore, radiolabeled ioninated compounds are found only in low concentrations in the blood, liver, spleen and intestines so that high contrast pictures can be obtained of the parts of the body which are high in calcium ion concentration. Furthermore, the iodinated-labeled compounds do not dissociate in vivo as shown by the lack of activity in the thyroid and the stomach after administration to an animal or a human. Furthermore, since the compounds of this invention can be radiolabeled either with iodine or technetium-99m, an investigator can document the metabolism of, for example, a bone metastases or a myocardial infarct, both initially and chronically, since radioactive iodine has a relatively long half-life. Therefore, the iodinated-radiolabeled compounds can be administered in order to monitor long term effects in vivo up to about 100 days or more, while compounds labeled with technetium-99m can be administered in order to monitor changes in vivo over a short period up to about 24 hours. Radiolabeling of the diphosphonic acid with technetium-99m can be conducted by admixing an acidic solution of $SnCl_2$ which is a reducing agent for pertechnetate with a buffered solution such as sodium and/or potassium phthalate, tartrate, gentisate, acetate, borate or mixtures thereof having a pH of between about 4.5 and about 8, preferably about 7. Preferably, the $SnCl_2$ is added to the buffered solution as a solution with concentrated HCl. Thereafter, the solution is neutralized such as with sodium hydroxide to attain a pH of between about 4.5 and about 8, preferably about 7. The diphosphonic acid then is added to the neutralized solution in an amount to attain a concentration of the diphosphonic acid at least about 5 mg up to a concentration where precipitation of the diphosphonic acid will occur. The resultant mixture then is allowed to incubate as for example at room temperature for about 10 minutes under an atmosphere of nitrogen or an inert gas. If desired, the solution can be moderately heated in order to reduce the incubation time. The solution then can be either freeze-dried and subsequently reconstituted for admixture with pertechnetate or can be admixed directly with pertechnetate solution to obtain the labeled diphosphonic acid. If desired, the resultant radiolabeled diphosphonic acid may be further purified to separate the labeled diphosphonic acid from free technetium such as by chromatography in a Sephadex column. This purification step is optional. In addition to the above, any conventional means for radiolabeling a compound with technetium-99m under reducing conditions can be utilized.

The diphosphonic acid compound can be radiolabeled with radioactive halogen including $I^{123}$, $I^{125}$, $I^{131}$ positron emitting $I^{126}$, $Br^{77}$, $Br^{82}$, or positron emitting $F^{18}$ by means known in the art, with minor modifications to concentration and volume. Iodination is conducted under oxidizing conditions utilizing reagents such as iodo mono chloride, Chloramine T or lactoperoxidase in the presence of diatomic radioactive iodine. The oxidizing agent promotes substitution of the aryl portion of the diphosphonic acid molecule either directly on the ring or on a substituent bound to the ring. A suitable method utilizing Chloramine T is described, for example, in Subramanian et al, Radiopharmaceutical, published Society Nuclear Medicine, 1975. A suitable method utilizing lactoperoxidase is shown, for example, in Morrison et al, Catalysis of Iodination by Lactoperoxidase, Biochemistry, 9, 2995–3000, 1970.

When utilizing iodo mono chloride, the following representative procedure can be used to form the radiolabeled diphosphonic acid. Radioactive diatomic iodine and iodo chloride are first equilibrated for about 15 minutes. Then a buffer such as a glycine buffer at a pH of between about 8.5 and about 9, usually about 9, is added. Thereafter, the diphosphonic acid is added to the buffer and reaction is allowed to continue until about 15 minutes. The resultant product then can be analyzed such as in a chromatographic column utilizing Sephadex to remove diatomic iodine and other inorganic salts. Utilizing this procedure, approximately 90% efficiency in radiolabeling is attained.

The present invention also provides a kit with which a user can prepare the compositions of this invention and administer them to a patient relatively quickly after preparation. It can include the aryl-methylene hydroxy diphosphonic acid in lyophilized form, frozen or liquid of suitable ionic strength and pH. In the case where it is desired to radiolabel with technetium-99m, the diphosphonic acid also may contain a reducing agent in admixture therewith or the reducing agent can be stored in a separate container in a form so that it can be admixed with the diphosphonic acid when it is desired to radiolabel. Representative suitable reducing agents are $SnCl_2$ or tin tartrate to be dissolved or already dissolved in an appropriate solution such as sodium acetate/acetic acid, deionized or distilled water or the like, such that a reducing pH of about 1 to 3 is obtained when admixed with technetium-99m as sodium pertechnetate. Therefore, technetium-99m as pertechnetate is either reduced in the presence of reducing agent prior to addition of the diphosphonic acid or is reduced when added to the diphosphonic acid containing the reducing agent. The solution of diphosphonic acid labeled with technetium-99m then is filtered (0.22μ) prior to patient administration.

In forming the technetium-labeled diphosphonic acid of this invention, a solution of the technetium-99m as the pertechnetate is poured onto the column in order to bind the technetium thereon. A physiologically acceptable aqueous solution of the diphosphonic acid then is poured onto the column in order to bind the labeled technetium to the diphosphonic acid. The labeled diphosphonic acid then is eluted from the column with saline or anotherwise appropriate buffer and is collected from the bottom of the column in a form suitable for intravenous administration to a patient. In an alternative embodiment, the eluted labeled disphosphonic acid is passed through a bed of anion exchange resin in order to remove free pertechnetate from the labeled diphosphonic acid thereby to form a pure labeled final diphosphonic acid suitably free of radiochemical contamination. If desired, these anion exchange resins need not be part of the columns utilized for labeling, but can comprise a separate bed through which the labeled diphosphonic acid is passed.

In an alternative embodiment of this invention, the kit can include a container for a column of material which entraps or otherwise binds reduced technetium-99m such as Sephadex, Sepharose or cellulose. The column of this material also can contain the reducing agent for technetium or the reducing agent can be added thereto when it is desired to reduce the technetium.

The present invention may also provide a kit which contains the diphosphonic acid either in lyophilized form, frozen or liquid of suitable ionic strength and pH. The diphosphonic acid is radiolabeled with $I^{123}$, $I^{125}$, $I^{126}$ or $I^{131}$ which is stored in a container either alone or in admixture with an oxidizing agent such as iodo chloride, Chloramine T, lactoperoxidase or the like. A buffer solution suitable for maintaining the pH of the diphosphonic acid and iodine when reacted at between about 8.5 and about 9.0 can be stored in a separate container or can be admixed with any one or all of the above reagents. The kit also optionally can contain a column or ion exchange material such as Sephadex or the like which is suitable for removing iodine salt and other inorganic salts from the labeled diphosphonic acid.

The labeled diphosphonic acid is administered such as by subcutaneous or intraarterial or by intravenous injection in a pharmaceutically acceptable saline solution, sterile and pyrogen-free. Suitable doses are usually between about 15 and about 25 mCi, preferably between about 20 and about 25 mCi of technetium-99m final diphosphonic acid for the normal 70 kg patient. A lesser amount is required when radioiodine is used, usually between about 0.2 and 0.5 mCi, preferably between about 0.4 and about 0.45 mCi for the normal 70 kg patient. The patient then can be scanned by conventional scintigraphy within about 2 hours to about 100 days after administration of the labeled diphosphonic acid. The portions of the body having a high concentration of calcium ion are located in those areas showing a high concentration of the labeled final diphosphonic acid.

The following example illustrates the present invention and is not intended to limit the same.

EXAMPLE I

The synthesis of ΦPA was accomplished with the procedure of Hendel and Cie, French Pat. No. 1,412,865. The nonhygroscopic ΦPA was obtained by treating benzoic acid with $H_2O$ and $PCl_3$ at 30°-40°C. The temperature was then raised to 110° C. and the mixture stirred for 2 hours. Thereafter, the reaction was cooled to 60° C. and mixed with EtOH. Volatile material was removed by distillation and the ΦPA salt was crystallized from the residue by the addition of water. Subsequent titration with NaOH yielded the sodium salt.

A stock solution was then prepared consisting of 16 mg ΦPA per cc of glycine buffer (pH=9.0).

The I-125 labeled ΦPA was formulated as follows:
a. I-125 (NaI): 1λ
b. ICl: 0λ
c. Glycine Buffer (pH=9.0): 15λ
d. ΦPA: 3.2 mg (200)
e. Glycine Buffer: 200λ

The I-125 and ICl were first equilibrated for 15 minutes prior to the addition of glycine buffer. The reaction was allowed to continue for 15 minutes after the addition of ΦPA. The product $$\left(\frac{3.2 \text{ mg } \Phi PA}{425}\right)$$

was de-salted over a G-25 Sephadex column and a portion of the eluant was assayed with ITLC in an acetone media and in chloroform: acetic acid (9:1). The final product was brought to 10 cc (0.320 mg ΦPA/cc) with glycine buffer and assayed for its content of I-125 radioactivity.

In Vivo Distribution and Retention of I-125-ΦPA

In vivo distribution and whole body retention studies of I-125 ΦPA were carried out in adult male (20-25 gm) Swiss Webster mice. The I-125 ΦPA in glycine buffer was diluted so that 0.032 mg was contained in 0.1 ml containing = 10 μCi (370 KBq) of radioiodine. Each animal received 0.1 ml via the tail vein. The mice (N=16) were counted immediately after injection in a whole body counter and periodically counted thereafter up to 100 days past post-administration. The whole body results were expressed graphically as the log of "% retained in whole body" as a function of "time (days)" after administration. In a separate study, 6 animals each were sacrificed at 1 hr, 47 hrs and 2 weeks, following IV administration and the content of activity determined in the blood, thyroid, liver, muscle, stomach, bone (femur, spine) bone marrow, heart, spleen, large intestine, small intestine and carcass. The tissue distribution results were expressed as the mean % D/gm±s.d. and % D/organ±s.d. These data were used to calculate the dosimetry of I-125 ΦPA using MIRD methodology, MIRD pamphlet No. 11, Society of Nuc. Med. 1975.

To obtain information relative to the imaging characteristics of I-125 labeled ΦPA, 100 μCi (0.32 mg/300 gms) was injected via the tail vein in 10 adult male Sprague-Dawley rats. Images were taken at various times after administration on a high resolution ¼" crystal, 19 PMT Gamma Camera, Nuclear Services, Inc. (LEAP collimator) and stored on disc with the aid of digital computer (HP-5407A). Imaging began immediately after injection and continued up to 30 days.

A pathological non-union fracture (tibia) was induced 8 days after injection in three of the rats and the rate of resorption of I-125 ΦPA was determined quantitatively via pinhole (3 mm) images from 2 hrs to 40 days post-fracture. Technetium-99m MDP images were also obtained at several times to measure new bone formation at the fracture sites. The data was digitized and expressed as:

$$\frac{\text{(I-125) } PA \text{ cts/matrix cell) FRACTURE}}{\text{(I-125) } PA \text{ cts/matrix cell) NORMAL}} \text{ and}$$

$$\frac{\text{(Tc-99}^m \text{ } MDP \text{ cts/matrix cell) FRACTURE}}{\text{(Tc-99}^m \text{ } MDP \text{ cts/matrix cell) NORMAL}}$$

Analytical data corresponding to the synthesis of PA and labeling of I-125 PA is summarized in Table I. The labeling efficiency was +80% (N=6) as determined by ITLC in acetone and in chloroform: acetic acid (9:1). The acetone shows the I-125 PA at the origin and the free I-125 at the solvent front, whereas the chloroform: acetic acid shows the free I-125 at the origin and the I-125 PA with a primary peak at Rf 0.8 and secondary peaks at Rf 0.4. The formulation was de-salted on a G-25 Sephadex column where the I-125 PA was eluted after the void volume with the free I-125 following.

The de-salted I-125 PA was administered intravenously in mice and rats. The time distribution studies showed a rapid skeletal uptake and retention of the tracer, with a minimal concentration in the blood, liver, spleen and intestine (Table 2A, Table 2B). Of interest is the lack of activity in the thyroid and stomach at all time periods, showing a substantial lack of in vivo deiodination of the agent. This is reflected in the dosimetry results in Table 3, with the bone being the critical organ (11.32 mR/μCi).

The whole body retention studies shows a triexponential excretion pattern of the I-125 ΦPA. Immediately after injection, 61.5% of the dose is excreted via the urine (T½b=9 days). After this time, the curve becomes monoexponential (33%, T½b=962d).

After the first 24 hours, there was essentially no change in the appearance of the whole body images. Good quality skeletal images were obtained up to 30 days after injection.

The I-125 ΦPA activity was reduced significantly after injury to bone. 5 days after the tibia was fractured in the rat relatively little I-125 activity remained at the fracture site relative to the normal tibia. A Tc-99$^m$ MDP scan done on day 5 post-fracture shows increased activity at the fracture sites. Similar results were obtained at 30 days. Table 4 shows quantitatively the $^{125}$I ΦPA loss and $^{99m}$Tc MDP uptake as a function of time after fracture.

These studies show that I-125 ΦPA concentrates in the skeleton of mice and rats following intravenous administration.

The long monoexponential release of I-125 ΦPA from bone (962 days) compares to that of Ba-133 in bone (1066 days). The whole body retention of $45_{Ca}$, $133_{Ba}$ and $85_{Sr}$ has been studied in rats where one day after a single IV injection, the retention of all 3 radionuclides was almost identical. Thereafter, the $^{85}$Sr tracer disappeared from the rat's body faster than that of $^{45}$Ca and $^{133}$Ba. The iodinated agent does behave comparable to the alkaline earth elements, particularly barium, as shown by its monoexponential release from the skeleton. This monoexponential release pattern was increased significantly in the rat tibia after inducement of a fracture. By 5 days, little of the $^{125}$I remained at the fracture site and concomitant $^{99}$Tc-MDP studies showed areas of increased activity at these sites. A similar pattern was observed at 30 days. This increased uptake corresponds to formation of new bony trabeculae (day 5) and remodeling (day 30), which is typical during fracture healing.

No toxic effects were observed in the animals studied that received a dose of 0.32 mg ΦPA/300 gm (rats) and 0.032 mg/20 gm (mice). Relative to a 70 kg person, this represents a safety factor of 74.7 and 112 respectively.

Tissue distribution studies showed <0.5% of the dose to concentrate in the thyroid, thus illustrating that $^{125}$I-ΦPA is not substantially de-iodinated in vivo. The critical organ, bone received 11.32 mR/μCi (Table 3). This radiation dose is relatively minute in comparison to that necessary to produce bone cancer from radium (50–100 rads).

The apparent affinity of the I-125 ΦPA to bone permits both short term and long term monitoring of changes in the skeletal structure. This compound is useful for measuring in vivo bone resorption rates for a variety of pathologies. The information obtained is of value for following bony metabolism in metabolic and metastatic diseased states as well as in the normal physiological condition.

TABLE I

Quality Control Data Corresponding to I-125 ΦPA

A. Elemental Analysis of PA (Na salt plus ~3 H$_2$O)

| Element | % Found | Calculated |
|---|---|---|
| C | 20.04 | 20.84 |
| H | 3.50 | 3.32 |
| P | 15.28 | 15.03 |

B. Labeling Efficiency ($\bar{m}$ for N = 6)

| 1. Acetone | | 2. Chloroform: acetic acid (9:1) | |
|---|---|---|---|
| a. origin | 83% | a. origin | 22% |
| b. middle | 79% | b. middle | 22% |
| c. solvent front | 10% | c. solvent front | 56% |

C. De-Salting with Sephadex G-25 (0.5 × 15 cm, 015 cc/min)

| Volume Phase | Characteristics |
|---|---|
| Void (2.25 cc) | Blue Dextran 2000 (peak volume = 0.7) |
| Fraction A (5 cc) | I-125 ΦPA |
| Fraction B (8 cc) | I-125 NaI |

TABLE 2

Tissue Distribution of I-125 ΦPA in Mice

| Organ | n = 6 % D/gm (±σ) 1 hr | | n = 6 % D/gm (±σ) 47 hrs | | n = 6 % D/gm (±σ) 336 hrs | |
|---|---|---|---|---|---|---|
| Blood | .564 | (.129) | .526 | (2.76 E-02) | 6.01 E-02 | (5.90 E-02) |
| Thyroid | 9.32 | (2.99) | 24.1 | (7.98) | 13.2 | (.437) |
| Liver | .889 | (.297) | .220 | (6.58 E-03) | .238 | (7.42 E-02) |
| Skeletal Muscle | .326 | (.191) | .124 | (.106) | .241 | (.268) |
| Stomach | 1.48 | (.854) | 7.65 | (2.30 E-02) | 4.08 E-02 | (2.93 E-02) |
| Bone (Femur) | 12.4 | (.572) | 13.3 | (3.38) | 12.5 | (3.39) |
| Bone (Spine) | 11.1 | (1.28) | 14.6 | (.48) | 12.9 | (.961) |
| Bone Marrow | | | 2.82 | (11.0) | 3.02 | (2.90) |
| Heart | | | .172 | (6.14 E-02) | .147 | (2.86 E-02) |
| Spleen | | | .103 | (5.62 E-02) | .388 | (3.78 E-02) |
| Large Intestine | | | .360 | (.164) | 8.23 | (4.53 E-02) |
| Small Intestine | | | 5.03 | (4.17 E-03) | 3.53 E-02 | (8.77 E-03) |
| Carcass | 2.16 | (.477) | .980 | (3.88 E-02) | 1.54 | (.285) |

| Organ | n = 6 % D/organ ±σ 1 hr. | | n = 6 % D/organ ±σ 47 hrs. | | % D/organ ±σ 336 hrs. | |
|---|---|---|---|---|---|---|
| Blood | 1.31 | (.327) | .148 | (7.72 E-02) | .171 | (.166) |
| Thyroid | .243 | (7.85 E-02) | .414 | (.147) | .338 | (.102) |
| Liver | 1.56 | (.295) | .465 | (8.36 E-02) | .431 | (7.66 E-02) |
| Skeletal Muscle | 4.79 | (2.71) | 2.00 | (1.75) | 1.35 | (.238) |
| Stomach | .845 | (.179) | 4.96 E-02 | (2.23 E-02) | 3.85 E-02 | (1.48 E-02) |
| Bone (Femur) | 41.3 | (1.35) | 47.3 | (12.8) | 44.5 | (13.7) |
| Bone (Spine) | 36.9 | (3.46) | 51.9 | (.241) | 40.1 | (.637) |
| Bone Marrow | | | .974 | (3.83) | 1.05 | (1.02) |
| Heart | | | 2.45 E-02 | (9.34 E-03) | 2.45 E-02 | (7.14 E-03) |
| Spleen | | | 2.09 | (1.13 E-02) | 4.76 E-02 | (7.83 E-03) |

TABLE 2-continued

| Tissue Distribution of I-125 ΦPA in Mice | | | | | |
|---|---|---|---|---|---|
| | | E-02 | | | |
| Large Intestine | | .393 | (.210) | 9.24 E-02 | (4.55 E-02) |
| Small Intestine | | .104 | (1.03 E-02) | 8.54 E-02 | (1.71 E-02) |
| Carcass | 39.1 (7.76) | 31.6 | (1.77) | 30.1 | (10.96) |

TABLE 3

| *Dosimetry of I-125 ΦPA mRads/microCi | |
|---|---|
| Organ | Self Dose Plus Contributions |
| Bone | 11.32 |
| Red marrow | 5.36 |
| Bladder wall** | 0.713 |
| Ovaries | 2.89 |
| Testes | 1.58 |
| Total body | 3.17 |

*Assume 35% bone, 5% total body, 60% urine
**Assume an effective half time of retention of 3 hrs.

TABLE 4

| $^{125}$I — ΦPA and $^{99m}$Tc-MDP Behavior In a Rat Tibia Fracture Model $\bar{m} \pm$ s.d. (N = 3) | | |
|---|---|---|
| ΔT | $\left(^{125}\text{I } \Phi\text{PA} \frac{\text{cts}}{\text{cell}}\right)$frac-ture / $\left(^{125}\text{I } \Phi\text{PA} \frac{\text{cts}}{\text{cell}}\right)$nor-mal | $\left(^{99m}\text{Tc MDP} \frac{\text{cts}}{\text{cell}}\right)$frac-ture / $\left(^{99m}\text{Tc MDP} \frac{\text{cts}}{\text{cell}}\right)$nor-mal |
| −2 days | *1.08 ± 0.035 | 1.05 ± 0.042 |
| +5 days | 0.628 ± 0.150 | 1.86 ± 0.375 |
| +20 days | 0.589 ± 0.009 | 3.49 ± 0.749 |
| +30 days | 0.474 ± 0.192 | 10.41 ± 1.61 |

*ratio of bone site before fracture to normal bone

We claim:

1. A composition of matter comprising a radiolabeled, with a radioisotope, diphosphonic acid, said diphosphonic acid represented by the formula:

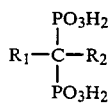

wherein: $R_1$ is aryl and is labeled with a halogen and $R_2$ is hydrogen, alkyl, alkenyl, amine, benzyl, hydroxyl, —CH$_2$PO$_3$H —CH$_2$CH$_2$PO$_3$H$_2$ and is labeled with halogen, said radiolabel selected from the group consisting of a radioactive halogen and both a radioactive halogen and a technetium-99m.

2. The composition of claim 1 wherein said diphosphonic acid is phenyl methylene hydroxy diphosphonic acid.

3. The composition of claim 1 wherein the diphosphonic acid is methylene hydroxyphenyl methylene hydroxy diphosphonic acid.

4. The composition of any one of claims 1, 2 or 3 wherein said radiolabel is both a radioactive halogen and technetium-99m.

5. The composition of any one of claims 1, 2 or 3 wherein said radiolabel is iodine-123.

6. The composition of any one of claims 1, 2 or 3 wherein said radiolabel is iodine-125.

7. The composition of any one of claims 1, 2 or 3 wherein said radiolabel is iodine-131.

8. The process for monitoring the metabolism of areas of the body having a high calcium ion concentration in a human which comprises injecting into the human the composition of claim 1 and monitoring the biodistribution of the labeled composition and resorptive rates of said agent from bony sites.

9. The process of claim 8 wherein said phosphonic acid is radiolabeled with both a radioactive halogen and technetium-99m.

10. The process of claim 8 wherein said phosphonic acid is radiolabeled with iodine-123.

11. The process of claim 8 wherein said phosphonic acid is radiolabeled with iodine-125.

12. The process of claim 8 wherein said phosphonic acid is radiolabeled with iodine-131.

13. A diagnostic kit suitable for forming a composition useful for monitoring areas of the body having a high calcium ion concentration which comprises a sterile package containing a diphosphonic acid of the formula:

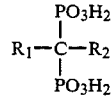

wherein: $R_1$ is aryl and is labeled with a halogen and $R_2$ is hydrogen, alkyl, alkenyl, amine, benzyl, hydroxyl, —CH$_2$PO$_3$H —CH$_2$CH$_2$PO$_3$H$_2$ and is labeled with halogen.

14. The kit of claim 14 wherein a physiologically acceptable reducing agent useful in reducing technetium (VII) to the technetium (IV) state is admixed with said diphosphonic acid.

15. The kit of claim 14 wherein said diphosphonic acid in said sterile package is lyophilized.

16. The kit of claim 14 which includes an ion exchange resin capable of purifying said radiolabeled composition.

* * * * *